(12) United States Patent
Zohar et al.

(10) Patent No.: US 10,136,621 B2
(45) Date of Patent: Nov. 27, 2018

(54) METHOD OF PRODUCING INFERTILE FISH AND EGG-PRODUCING AQUATIC ANIMALS AND OF DELIVERING COMPOUNDS INTO EGGS AND EMBRYOS

(71) Applicant: University of Maryland Baltimore County, Baltimore, MD (US)

(72) Inventors: Yonathan Zohar, Baltimore, MD (US); Ten-Tsao Wong, Timonium, MD (US)

(73) Assignee: UNIVERSITY OF MARYLAND BALTIMORE COUNTY, Baltimore, MD (US)

( * ) Notice: Subject to any disclaimer, the term of this patent is extended or adjusted under 35 U.S.C. 154(b) by 0 days.

(21) Appl. No.: 16/011,631

(22) Filed: Jun. 18, 2018

(65) Prior Publication Data
US 2018/0288984 A1    Oct. 11, 2018

Related U.S. Application Data

(63) Continuation of application No. 15/035,342, filed as application No. PCT/US2014/065698 on Nov. 14, 2014, now Pat. No. 9,999,208.

(60) Provisional application No. 62/050,815, filed on Sep. 16, 2014, provisional application No. 61/968,458, filed on Mar. 21, 2014, provisional application No. 61/904,652, filed on Nov. 15, 2013.

(51) Int. Cl.
| | | |
|---|---|---|
| C07H 21/02 | (2006.01) | |
| C07H 21/04 | (2006.01) | |
| A61K 31/70 | (2006.01) | |
| A01K 67/027 | (2006.01) | |
| C12N 15/873 | (2010.01) | |
| C12N 15/113 | (2010.01) | |
| C12N 5/00 | (2006.01) | |

(52) U.S. Cl.
CPC ........ *A01K 67/0276* (2013.01); *C12N 15/113* (2013.01); *C12N 15/873* (2013.01); *A01K 2207/05* (2013.01); *A01K 2217/075* (2013.01); *A01K 2227/40* (2013.01); *A01K 2267/02* (2013.01); *C12N 2310/11* (2013.01); *C12N 2310/3233* (2013.01); *C12N 2310/351* (2013.01); *Y02A 90/40* (2018.01)

(58) Field of Classification Search
None
See application file for complete search history.

(56) References Cited

U.S. PATENT DOCUMENTS

| | | |
|---|---|---|
| 7,194,978 B2 | 3/2007 | Zohar et al. |
| 7,935,816 B2 | 5/2011 | Li |
| 2005/0132969 A1 | 6/2005 | Zohar et al. |
| 2010/0212039 A1 | 8/2010 | Wu et al. |
| 2014/0261212 A1 | 9/2014 | Peterson et al. |

FOREIGN PATENT DOCUMENTS

| | | |
|---|---|---|
| EP | 2535404 A1 | 12/2012 |
| WO | 2005001028 A2 | 1/2005 |
| WO | 2009055027 A2 | 4/2009 |
| WO | 2012106026 A2 | 8/2012 |
| WO | 2013054123 A1 | 4/2013 |
| WO | 2015073819 A1 | 5/2015 |
| WO | 2016187198 A2 | 11/2016 |

OTHER PUBLICATIONS

Zohar, Y., et al., "Method of Producing Infertile Fish and Egg-Producing Aquatic Animals and of Delivering Compounds Into Eggs and Embryos", May 9, 2016.
Abraham, E., et al., "Targeted Gonadotropin-Releasing Hormone-3 Neuron Ablation in Zebrafish: Effects on Neurogenesis, Neuronal Migration, and Reproduction", "Endocrinology", Oct. 27, 2009, pp. 332-340, vol. 151.
Chen, C., et al., "Chorion microstructure for identifying five fish eggs of Apogonidae", "Journal of Fish Biology", Aug. 21, 2007, pp. 913-919, vol. 71.
Ciruna, B., et al., "Production of maternal-zygotic mutant zebrafish by germ-line replacement", "PNAS", Nov. 12, 2002, pp. 14919-14924, vol. 99, No. 23.
Cotelli, F., et al., "Structure and Composition of the Fish Egg Chorion (*Carassius auratus*)", "Journal of Ultrasructure and Molecular Structure Research", Apr. 1988, pp. 70-78, vol. 99.
Fujimoto, T., et al., "Sexual dimorphism of gonadal structure and gene expression in germ cell-deficient loach, a teleost fish", "PNAS", Oct. 5, 2010, pp. 17211-17216, vol. 107, No. 40.
Gellert, G., et al., "Effect of age on the susceptibility of zebrafish eggs to industrial wastewater.", "Water Res.", Oct. 2001, pp. 3754-3757, vol. 35, No. 15.
Hagedorn, M., et al., "Water Distribution and Permeability of Zebrafish Embryos, Brachydanio rerio", "The Journal of Experimental Zoology", 1997, pp. 356-371, vol. 278.

(Continued)

*Primary Examiner* — Sean McGarry
(74) *Attorney, Agent, or Firm* — Hultquist, PLLC; Steven J. Hultquist (57) ABSTRACT

Methods for the production of reproductively sterile fish and aquatic animals for aquaculture, the aquarium trade, and control of invasive species are described. The methods include disruption of gonadal development through the administration of compounds that lead to the failure of fertile gonadal development. Compounds may be delivered to the eggs prior to fertilization or water activation or post fertilization and water activation by contacting unfertilized or pre-water-activated fertilized eggs or fertilized eggs in an immersion medium including the compound of interest. Compounds may be conjugated with a molecular transporter compound effective for chorionic transport of the conjugate. The compounds may be antisense Morpholino oligomers that are capable of effectively suppressing the expression of the dead end gene or other essential genes for germ cell development in fish and other egg-producing aquatic animals.

22 Claims, 9 Drawing Sheets

Specification includes a Sequence Listing.

(56) References Cited

OTHER PUBLICATIONS

Hu, W., et al., "Antisense for gonadotropin-releasing hormone reduces gonadotropin synthesis and gonadal developement in transgenic common carp (*Cyprinus carpio*)", "Aquaculture", 2007, pp. 498-506, vol. 271.

Kais, B., et al., "DMSO Modifies the Permeability of the Zebrafish (*Danio rerio*) chorion-Implications for the Fish Embryo Test (FET)", "Aquatic Toxicology", May 28, 2013, pp. 229-238, vol. 140-141.

Li, Y., et al., "Design and Synthesis of Dendritic Molecular Transporter that Achieves Efficient in Vivo Delivery of Morpholino Antisense Oligo", "Bioconjugate Chemistry", Jun. 20, 2008, pp. 1464-1470, vol. 19, No. 7.

Morcos, P., et al., "Vivo-Morpholinos: A non-peptide transporter delivers Morpholinos into a wide array of mouse tissues", "BioTechniques", Dec. 2008, pp. 613-623, vol. 45.

Pantos, A., et al., "Guanidinium Group: A Versatile Moiety Inducing Transport and Multicompartmentalization in Complementary Membranes", "Biochimica et Biophysica Acta", Dec. 12, 2007, pp. 811-823, vol. 1778.

Skugor, A., et al., "Knockdown of the Germ Cell Factor Dead End Induces Multiple Transcriptional Changes in Atlantic Cod (*Gadus morhua*) Hatchlings", "Animal Reproductive Science", Dec. 31, 2013, pp. 129-137, vol. 144.

Slanchev, K., et al., "Development without germ cells: the role of the germ line in zebrafish sex differentiation", "PNAS", Mar. 15, 2005, pp. 4074-4079, vol. 102, No. 11.

Slanchev, K., et al., "Control of dead end localization and activity implications for the function of the protein in antagonizing miRNA function", "Mechanisms of Development", Oct. 25, 2008, pp. 270-277, vol. 126.

Terner, C., "Studies of Metagolism in Embronic Development—I. The Oxidative Metabolism of Unfertilized and Embryonated Eggs of the Rainbow Trout", "Comp. Biochem. Physiol.", Mar. 1968, pp. 933-940, vol. 24 .

Theodossiou, T.A., et al., "Guanidinylated Dendritic Molecular Transporters: Prospective Drug Delivery Systems and Application in Cell Transfection", "ChemMedChem", Nov. 4, 2008, pp. 1635-1643, vol. 3.

Weidinger, G., et al., "dead end, a Novel Vertebrate Germ Plasm Component, Is Required for Zebrafish Primordial Germ Cell Migration and Survival", "Current Biology", Aug. 19, 2003, pp. 1429-1434, vol. 13.

Wender, P., et al., "The Design of Guanidinium-Rich Transporters and Their Internalization Mechanisms", "Advanced Drug Delivery Reviews", Dec. 31, 2007, pp. 452-472, vol. 60.

Wong, T.T., et al., "Production of Reproductively Sterile Fish by a Non-Transgenic Gene Silencing Technology", "Scientific Reports", Oct. 29, 2015, vol. 5, No. 15822.

Wong, T.T., et al., "Production of Reproductively Sterile Fish: a Mini-Review of Germ Cell Elimination Technologies", "General and Comparitive Endrocrinology", Jan. 9, 2015, pp. 3-8, vol. 221.

Wong, T., et al., "Inducible Sterilization of Zebrafish by Disruption of Primordial Germ Cell Migration", "PLOS One", Jun. 2013, pp. e68455 (1-8), vol. 8, No. 6.

Xu, Jing, et al., "Defining Global Gene Expression Changes of the Hypothalamic-Pituitary-Gonadal Axis in Female sGnRHAntisense Transgenic Common Carp (*Cyprinus carpio*)", "PLoS One", Jun. 2011, pp. e 21057 (12 pages), vol. 6, No. 6.

SEQUENCE LISTING

<160> NUMBER OF SEQ ID NOS: 5

<210> SEQ ID NO 1
<211> LENGTH: 25
<212> TYPE: DNA
<213> ORGANISM: Salmo salar

<400> SEQUENCE: 1
ctgacttgaa cgctcctcca ttatc                                    25

<210> SEQ ID NO 2
<211> LENGTH: 18
<212> TYPE: DNA
<213> ORGANISM: Salmo salar

<400> SEQUENCE: 2
acttgaacgc tcctccat                                            18

<210> SEQ ID NO 3
<211> LENGTH: 25
<212> TYPE: DNA
<213> ORGANISM: Morone saxatilis

```
<400> SEQUENCE: 3
ggctctgctt gctctccatc atctc                                              25

<210> SEQ ID NO 4
<211> LENGTH: 25
<212> TYPE: DNA
<213> ORGANISM: Oreochromi niloticus

<400> SEQUENCE: 4
ctggctttgc gtgttttcca tcgtc                                              25

<210> SEQ ID NO 5
<211> LENGTH: 25
<212> TYPE: DNA
<213> ORGANISM: Danio rerio

<400> SEQUENCE: 5
gctgggcatc catgtctccg accat                                              25
```

METHOD OF PRODUCING INFERTILE FISH AND EGG-PRODUCING AQUATIC ANIMALS AND OF DELIVERING COMPOUNDS INTO EGGS AND EMBRYOS

CROSS-REFERENCE TO RELATED APPLICATIONS

This is a continuation under 35 USC § 120 of U.S. patent application Ser. No. 15/035,342 filed May 9, 2016, and issued Jun. 19, 2018 as U.S. Pat. No. 9,999,208, which in turn is a U.S. national phase under the provisions of 35 U.S.C. § 371 of International Patent Application No. PCT/US14/65698 filed Nov. 14, 2014, which in turn claims benefit of priority under the provisions of 35 USC § 119 of U.S. Provisional Application No. 61/904,652 filed Nov. 15, 2013, U.S. Provisional Application No. 61/968,458 filed Mar. 21, 2014, and U.S. Provisional Application 62/050,815 filed Sep. 16, 2014. The disclosures of U.S. patent application Ser. No. 15/035,342, International Patent Application No. PCT/US14/65698, U.S. Provisional Application No. 61/904,652, U.S. Provisional Application No. 61/968,458, and U.S. Provisional Application 62/050,815 are hereby incorporated herein by reference in their respective entireties, for all purposes.

TECHNICAL FIELD

This disclosure relates to methods for the production of reproductively sterile fish and other egg-producing aquatic animals for aquaculture, the aquarium trade, and control of invasive species. The methods include disruption of gonadal development through the administration of compounds that lead to the failure of fertile gonadal development. Such compounds may be delivered to the eggs prior to or after fertilization (or water activation) by contacting unfertilized or fertilized eggs with a compound of interest.

BACKGROUND ART

Aquaculture is becoming increasingly important to resolve the current and projected global shortfalls in aquatic foods and seafood availability. As the shift in dependence from fisheries' harvests to artificially propagated aquatic species continues, optimization of aquaculture methods is increasingly necessary to maximize food production and minimize ecological impact, thereby achieving long-term environmental sustainability of our seafood supplies.

Sterilization (induced infertility) of farmed fish and other egg-producing aquatic animals enhances their growth rate by increasing the conversion of food energy to muscle growth, instead of gonadal development. In addition, if escaped from aquaculture operations to the environment, reproductively sterile farmed fish and other egg-producing aquatic animals, including domesticated, non-native or genetically modified species, will not be able to reproduce or inter-breed with wild population. This will assist biological containment and prevent genetic contamination of wild populations and/or the establishment in the wild of domestic, non-native or genetically modified farmed fish and other egg-producing aquatic animals.

Additionally, reproductive sterilization of fish and other egg-producing aquatic animals prevents unauthorized breeding and sale of patented, or otherwise protected, genetically selected or modified fish and other egg-producing aquatic animals.

SUMMARY

The disclosure relates to methods of producing populations of sterile egg-producing aquatic animals, wherein the sterilization methods include disruption of primordial germ cell migration and/or development in each treated individual without detrimentally affecting other characteristics of a normal animal.

One aspect of the disclosure relates to a method for producing reproductively sterile egg-producing aquatic animals, said method comprising contacting unfertilized egg(s) or fertilized egg(s) prior to water activation with anti-sense Morpholino oligomer that is effective to transfect the egg(s) and render individual(s) produced therefrom reproductively sterile.

Yet another aspect of the disclosure relates to a method for producing reproductively sterile egg-producing aquatic animals, said method comprising contacting unfertilized egg(s) or fertilized egg(s) prior to water activation with anti-sense Morpholino oligomer that is effective to transfect the egg(s) and render individual(s) produced therefrom reproductively sterile, wherein the antisense Morpholino oligomer is conjugated with a molecular transporter compound effective for chorionic transport of the conjugate. The molecular transporter compound may for example comprise an octaguanidine dendrimer comprising a triazine core moiety.

In another aspect, the disclosure relates to a method for producing reproductively sterile egg-producing aquatic animals, said method comprising contacting fertilized egg(s) with anti-sense Morpholino oligomer conjugated with a molecular transporter compound that is effective to transfect the fertilized egg(s) and render individual(s) produced therefrom reproductively sterile.

In a further aspect of the disclosure, a method for delivery of compounds into egg(s) from egg-producing aquatic animals is provided comprising contacting unfertilized or pre-water-activated egg(s) with a biologically beneficial compound or a conjugate of a biologically beneficial compound and a molecular transporter compound comprising an octaguanidine dendrimer comprising a triazine core moiety.

An additional aspect of the disclosure relates to a composition for treatment of fish egg(s) to render fish produced therefrom reproductively sterile, said composition comprising an anti-sense Morpholino oligomer comprising an oligomer selected from the group consisting of oligomers of SEQ ID NOS: 1-4 and variants thereof that are effective in reproductively sterilizing fish upon contact with fish egg(s).

In a further aspect, the disclosure relates to a composition wherein the antisense Morpholino oligomer is conjugated with a molecular transporter compound effective for chorionic transport of the conjugate, wherein the molecular transporter compound comprises an octaguanidine dendrimer comprising a triazine core moiety.

Other aspects, features and advantages of the invention will be more fully apparent from the ensuing disclosure and appended claims.

BRIEF DESCRIPTION OF THE DRAWINGS

3A, uncharacterized aggregates were found in fish embryos after 3 hour immersion with 20 μM zfdnd-MO-Vivo. In FIG. 3B, more aggregates appeared after 5 hour immersion. In FIG. 3C and FIG. 3D, aggregates were not found in the embryos immersed with 20 μM zfdnd-MO for (3C) 3 hours and (3D) 5 hours (without Vivo).

FIG. 4A shows that in control fish, germ cells migrated to the gonadal region and maintained their morphology. FIG. 4B shows that treatment of zfdnd-MO-Vivo caused germ cell mis-migration and eventually differentiated into other cell types.

FIG. 5A shows no difference in appearance or overall size observed between treated adult fish and wild-type males. FIG. 5B shows no significant difference in body-weight of 3-month-old fish (n=12 by random sampling) among zfdnd-MO-Vivo treated fish, and untreated wild-type males.

(FIG. 6B) well-developed ovary of untreated female fish; (FIG. 6C) the gonads of zfdnd-MO-Vivo treated fish developed into a thin filament-like tissue. Photomicrographs (6D-6F) show (FIG. 6D) active spermatogenesis of the testis of untreated male fish; (FIG. 6E) a well-developed ovary of an untreated female fish with oocytes at different developmental stages; (FIG. 6F) the gonad of treated fish appears to be under-developed and surrounded with a large amount of adipocytes without advanced gonadal structure or germ cells.

FIG. 10 illustrates the portion of the fish used for RNA extraction and the results obtained. Salmonids (trout) eggs were immersed with salmonid's dnd-MO at A: Control; B: 10 μM Ssdnd-MO; C: 10 μM Ssdnd-MO+1 μM Ssdnd-MO-Vivo; D: 10 μM Ssdnd-MO+2 μM Ssdnd-MO-Vivo for 48 hours before fertilization. When eggs were treated with 10 μM Ssdnd-MO+1 μM Ssdnd-MO-Vivo or 10 μM Ssdnd-MO+2 μM Ssdnd-MO-Vivo, germ cells were eliminated indicated by the lack of expression of germ cell specific maker gene vasa

DETAILED DESCRIPTION OF THE DISCLOSURE

The present disclosure relates in one aspect to the delivery of beneficial compounds to eggs from fish or other egg-producing aquatic animals by contacting the eggs with the compounds prior to fertilization or water activation. Delivery of beneficial compounds into fish or other egg-producing aquatic animals has traditionally been achieved via the feed, injection, or immersion of embryos or individuals in a compound of interest. Injection of stock, however, is not practical in large-scale commercial aquaculture operations. In addition, use of immersion treatment of fertilized and water-activated eggs has been limited, due to low permeability of the chorion of the egg, a thick acellular multi-layer coat, also known as the egg envelope, composed mainly of proteins and glycoproteins. Typically, in immersion treatment of fish or other egg-producing aquatic animal embryos, large molecular compounds are not able to traverse the chorion and reach the embryo.

After ovulation/spawning and prior to fertilization and water-activation, eggs have a permeable and perforated chorion (or outermost coat) that allows for entry of water and substances into the unfertilized eggs through the pores or the micropyle, a small canal in the chorion of the egg allowing for the sperm to penetrate the egg for fertilization. Following fertilization and water-activation, the chorion becomes sealed and the egg is rendered impermeable, preventing further uptake of substances or water from the environment.

As has been discovered, during the window of time between ovulation/spawning and fertilization/water-activation, the eggs are permeable and uptake of compounds from immersion media into the eggs is efficient. Following a short period of immersion, the eggs are fertilized and water-activated at which time they become impermeable and start embryonic development.

The present disclosure in some aspects describes methods for efficiently delivering compounds into eggs of egg-producing aquatic animals by contacting the eggs with compounds of interest during a window of time when the eggs are permeable to environmental substances, i.e., after ovulation/spawning and before fertilization or after fertilization and before water activation. In various embodiments, the contacting comprises immersion of the eggs in an immersion medium containing one or more compound(s) of interest.

Accordingly, in various aspects, the present disclosure relates to contacting unfertilized eggs or fertilized eggs prior water-activation with a compound in immersion media. The compound used in the immersion media may contribute to the sterilization of the egg-producing aquatic animals, and the immersion medium in specific embodiments may include additional compounds or other materials that are beneficial to the egg-producing aquatic animals hatched from eggs contacted with the immersion medium, e.g., materials such as DNA/RNA, hormones, growth promoters, protective antigens, nutrients, etc.

The disclosure thus contemplates methods of producing reproductively sterile egg-producing aquatic animals involving contacting eggs in immersion medium with selected compounds resulting in reproductively sterile individuals. The sterilization methods comprise the disruption of gonadal development in the embryo. The present disclosure also relates to methods of preventing interbreeding between domesticated, non-native and genetically modified farmed fish/other egg-producing aquatic animals and their wild stocks, as well as to the establishment of such aquacultured fish and other egg-producing aquatic animals in the wild. In addition, the disclosed methods may be employed to enable prevention of genetic contamination of a wild population by farmed fish and other egg-producing aquatic animals.

The methods of the disclosure are applicable to egg-producing aquatic animals. As used herein, egg-producing aquatic animals include egg-bearing species of water-based animals including all fish species and other egg-producing aquatic animals such as crustaceans and/or mollusks.

Accordingly, egg-producing aquatic animals includes all fish species, including, but not limited to, salmon, Atlantic salmon, coho salmon, chinook salmon, chum salmon, sockeye salmon, pink salmon, masu salmon, trout, rainbow trout, brook trout, brown trout, common grayling, Arctic grayling, Arctic char, bass, hybrid bass, striped bass, white bass, striped-white bass hybrids, yellow bass, perch, white perch, yellow perch, European perch, bass-perch hybrids, Nile tilapia, blue tilapia, blue-Nile tilapia hybrids, Mozambique tilapia, zebrafish, carp species, breams, seabreams, porgies, catfish species, and cod.

The methods of the disclosure are additionally applicable to egg-producing aquatic animals such as crustaceans and/or mollusks. Such egg-producing aquatic animals may include, but are not limited to, shrimp, prawn, lobster, crayfish, crabs, oysters, squid, octopus, and the like.

As defined herein, "sterilizing" egg-producing aquatic animals is understood to mean rendering an individual unable to sexually reproduce. Reproductively sterile egg-producing aquatic animals are defined as individuals that are unable to reach sexual maturity or to reproduce when reaching the age of sexual maturity.

The methods of producing a reproductively sterile fish and other egg-producing aquatic animals include administration of compounds to their eggs prior to fertilization or water-activation to disrupt gonadotropin releasing hormone (GnRH) cell development and/or primordial germ cell (PGC) development, migration and colonization in the gonad of the embryo, which results in failure of gonad development and/or failure of full and proper gonadal functioning at the cellular or tissular level, and ultimately the generation of sterile fish and other egg-producing aquatic animals.

GnRH is required for gonadal development and the maintenance of reproductive cycles in vertebrates. Specifically, GnRH, also known as luteinizing hormone releasing hormone (LHRH), stimulates the synthesis and secretion of the gonadotropins, in particular follicle-stimulating hormone (FSH) and luteinizing hormone (LH), that are essential to gonadal development and, therefore, disruption of the synthesis and secretion of GnRH is a potent method to induce sterility.

PGCs are a population of cells in the fish embryo that are precursors of the gametes of the adult fish and other egg-producing aquatic animals. The PGCs are produced during the very early stages of embryonic development. At later stages of embryonic development, the PGCs migrate through the embryo from their original location to the area of the gonadal precursors. At the end of their migration, the PGCs enter the developing gonads, colonize the tissue and start the process of gametogenesis, leading to mature gonads in the adult fish and other egg-producing aquatic animals.

The methods of the disclosure allow generation of reproductively sterile (infertile) egg-producing aquatic animals. The sterilization strategy will specifically disrupt gonad development in the individuals without detrimentally affecting any other characteristics resulting in the production of completely normal but reproductively sterile egg-producing aquatic animals.

Figure 1:
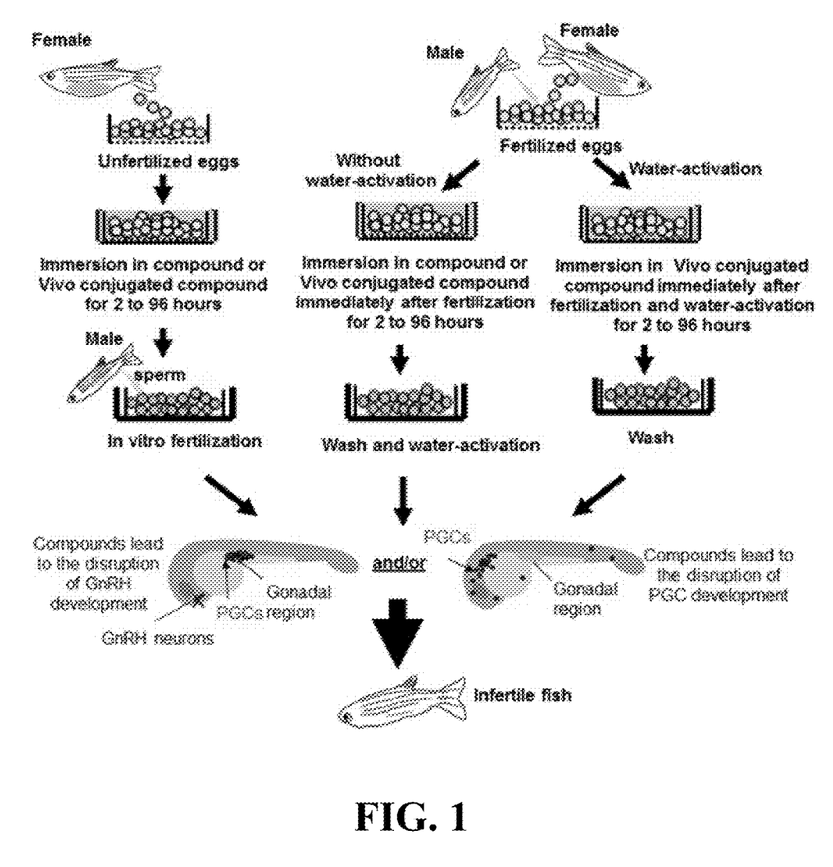
FIG. 1 is flow chart diagram of an immersion method according to embodiments of the disclosure.

FIG. 1 is a diagram of the immersion method of embodiments of the disclosure. As shown, compounds are delivered to the eggs by immersing unfertilized eggs (or pre-water-activated eggs) or fertilized eggs in the compounds of interest in an immersion media. Typically, the eggs are immersed in the compound for about 2 to about 96 hours or more depending on the species and immersion temperature. The administration of the compound will preferably take place while the chorion of the eggs is permeable. The treatment with the compounds of interest will result in early stage embryos having disruption of GnRH development or PGC development. When eggs are treated by the immersion process, the resulting adult fish and other egg-producing aquatic animals will be reproductively infertile or sterile, typically having no fertile gonadal development.

Thus, in various embodiments, the disclosure provides a method to efficiently administer compounds into embryos by contacting eggs with compounds prior to fertilization or water-activation. The selected compounds disrupt GnRH cell and/or PGC development, migration and/or survival in large numbers of embryos, resulting in large-scale production of reproductively sterile adult fish and other egg-producing aquatic animals. The methods of the disclosure are also applicable to single embryos in smaller scale production of reproductively sterile adult fish and other egg-producing aquatic animals.

The compounds for use in the methods of the disclosure may include compounds known to disrupt GnRH cell and/or PGC development, migration and/or survival which are capable of entering the chorion of a pre-fertilized or a pre-water-activated egg. In one aspect, such compound may be an antisense Morpholino oligomer capable of the disruption of a GnRH cell and/or PGC development and capable of traversing the chorion of eggs. Thus, antisense Morpholino oligomer useful in the methods of the disclosure is anti-sense Morpholino oligomer that is effective to transfect the egg(s) and render individual(s) produced therefrom reproductively sterile.

Antisense Morpholino oligomer is used to transiently silence gene expression by either blocking translation or RNA splicing that is an essential step to generate mRNA. Specific antisense Morpholino oligomers can be identified to transiently block or suppress the expression of genes that are essential for embryonic germ cell development including but not limited to deadend, nanos, vasa, gnrh or fsh receptor which results in the failure of gonadal development and ultimately generates sterile fish and other egg-producing aquatic animals.

Thus, in one aspect of the disclosure, a method for producing reproductively sterile egg-producing aquatic animals is provided comprising contacting unfertilized egg(s) or pre-water-activated fertilized eggs with anti-sense Morpholino oligomer that is effective to transfect the egg(s) and render individual(s) produced therefrom reproductively sterile. The contacting comprises chorionic transfection of the egg(s).

In such aspect, the disclosure relates to methods of producing reproductively sterile egg-producing aquatic animals by administration of effective Morpholino oligomers to eggs in order to disrupt primordial germ cell (PGC) development, and migration to, and colonization in, the gonad of the embryo, which results in the failure of gonad development and/or full and proper gonadal functioning at the cellular or tissular level, and ultimately the generation of sterile fish.

Dead end (dnd) is a vertebrate-specific component of the germ plasm and germ-cell granules that is essential for germ cell development in certain fish. The dnd gene is specifically expressed in germ plasm and primordial germ cells. Since dnd is considered essential for normal migration and survival of PGCs, embryos devoid of this protein develop to become sterile adults.

The disclosed methods are useful for the production of reproductively sterile fish and other egg-producing aquatic animals for aquaculture, the aquarium trade, and control of invasive species. In one aspect, the methods include disruption of gonadal development through the administration of antisense Morpholino oligomer against dead end mRNA (dnd-MO) or other genes that are essential to gonadal development including, but not limited to, nanos, vasa, gnrh or fsh receptor, to pre-fertilized or pre-water-activated egg(s). The action of dnd-MO or other antisense Morpholino oligomer against genes that are essential to gonadal development leads to the failure of fertile gonad development and to sterile adult fish.

In embodiments, the dnd-MO is able to transiently suppress expression of dead end protein that is essential for embryonic germ cell development.

The present disclosure also relates to specific Morpholino oligomer sequences for use in methods for suppression of expression a dead end gene in a fish.

Figure 2:
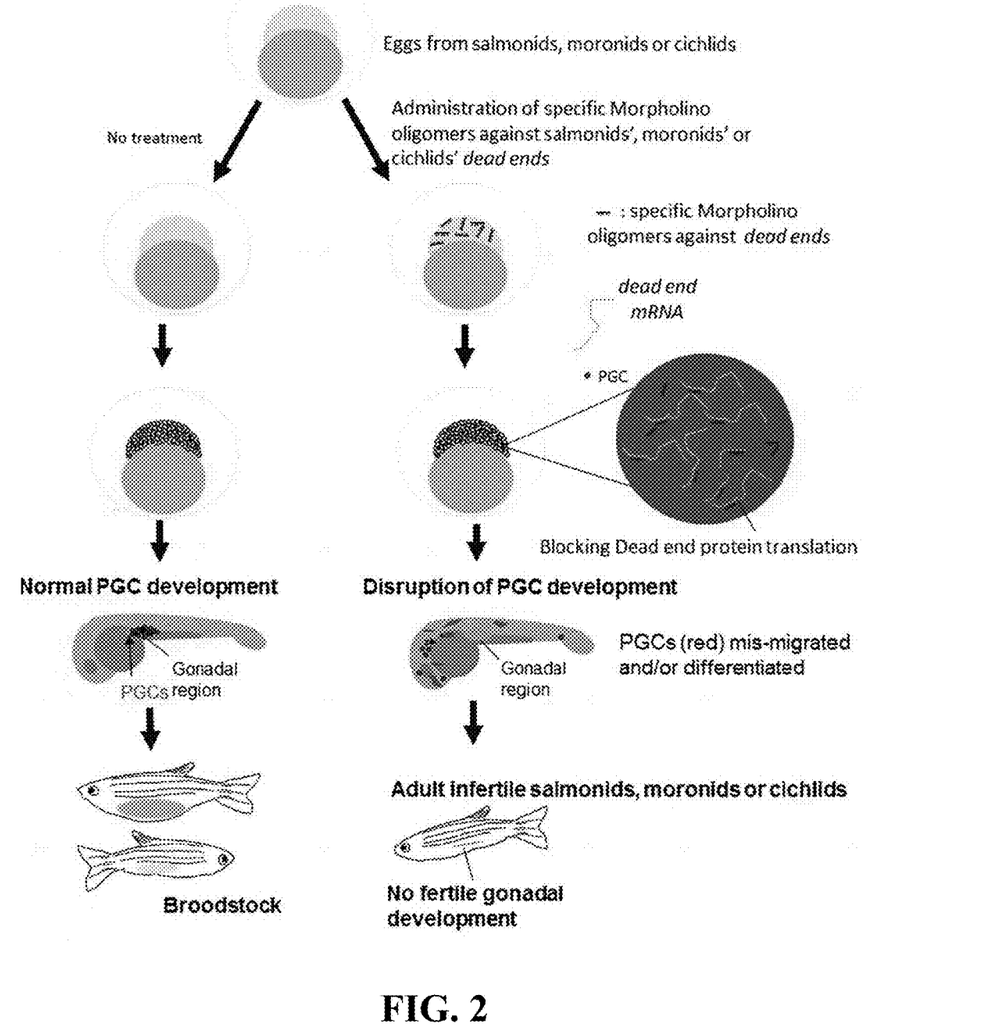
FIG. 2 is a flow chart diagram of the production of reproductively sterile fish obtained according to other embodiments of the disclosure.

FIG. 2 is a flow chart for production of reproductively sterile fish by the administration of specific Morpholino oligomers against the dead end mRNAs of salmonids, moronids or cichlids to disrupt primordial germ cell (PGC) development, which results in the failure of gonad development, and ultimately the generation of sterile fish. When eggs are not treated with Morpholino oligomers, they may become fertile broodstock.

As shown in FIG. 2, eggs from salmonids, moronids or cichlids, or other fish species, may be contacted with Morpholino oligomers against the dead end genes of the relevant fish species. FIG. 2 illustrates the administration of specific Morpholino oligomers against the dead end genes of salmonids, moronids or chichlids. Alternatively, the eggs may be given no treatment. As shown, where the unfertilized eggs are contacted with Morpholino oligomers, oligomers effect the suppression of or blocking of Dead end protein translation, resulting in the disruption of PCG development. The adult salmonids, monoids or cichlids are consequently infertile, since there is no fertile gonadal development. When normal PGC development is permitted, the fish will have normal fertile gonadal development and the fish may be used as broodstock.

Thus, in embodiments, the antisense Morpholino oligomers are capable of effectively suppressing expression of at least one of Salmonidae dead end gene, Moronidae dead end gene or cichlidae dead end gene.

In another aspect, the disclosure relates to the identification of specific sequences of Morpholino oligomers that can be used to transiently suppress the expression of specific genes that are essential for germ cell development. In another aspect, the disclosure relates to specific antisense Morpholino oligomers that are able to transiently and effectively suppress the translation of Dead end, an essential protein for germ cell survival, and specifically disrupt gonadal development resulting in the production of infertile fish, e.g., salmonids (salmons and trouts), moronids (basses) and cichlids (tilapias and ornamental cichlids).

In another aspect, the disclosure relates to a specific Morpholino oligomer, 5'-CTGACTTGAACGCTCCTC-CATTATC-3' (SEQ ID NO: 1) and its variants, e.g., 5'-ACT-TGAACGCTCCTCCAT-3' (SEQ ID NO: 2), that are able to transiently and effectively suppress the expression of Salmonidae dead end gene, which results in the failure of gonad development and/or the failure of full and proper gonadal functioning, and ultimately the generation of sterile salmonids. Accordingly, the methods of the disclosure are applicable to all salmonids, including, but not limited to, Atlantic, coho, chinook, chum, sockeye, pink and masu salmons, rainbow, brook and brown trouts, common and Arctic grayling, and Arctic charr, among others.

In another aspect, the disclosure relates to a specific Morpholino oligomer, 5'-GGCTCTGCTTGCTCTCCAT-CATCTC-3' (SEQ ID NO: 3) and its variants that are able to transiently and effectively suppress the expression of Moronidae dead end gene, which results in the failure of gonad development and/or full and proper gonadal functioning, and ultimately the generation of sterile moronids. Accordingly, the methods of the disclosure are applicable to all moronids including, but not limited to, striped bass, white bass, striped-white bass hybrids, yellow bass, white perch, yellow perch, European perch, and bass-perch hybrids, among others.

In another aspect, the disclosure relates to a specific Morpholino oligomer, 5'-CTGGCTTTGCGTGTTTTC-CATCGTC-3' (SEQ ID NO: 4) and its variants that are able to transiently and effectively suppress the expression of cichlidae dead end gene, which results in the failure of gonad development and/or the failure of full and proper gonadal functioning, and ultimately the generation of sterile cichlids. Accordingly, the methods of the disclosure are applicable to all cichlid and tilapia species, including, but not limited to, Nile tilapia, blue tilapia, blue-Nile tilapia hybrids, Mozambique tilapia, and other edible and ornamental cichlid species and their hybrids.

The Morpholino oligomers may be variants of the listed sequences. These variations may include but not be limited to other modified nucleic acids and other Morpholino oligomers that cover the whole or partial sequences listed above. Particularly included are antisense oligomers that comprise, consist essentially of, or consist of, one or more of SEQ ID NOS:1, 3 and 4. Also included are variants of these antisense oligomers, including variant oligomers having 80%, 85%, 90%, 95%, 97%, 98%, or 99% (including all integers in between) sequence identity or sequence homology to any one of SEQ ID NOS: 1, 3 and 4, and/or variants that differ from these sequences by about 1, 2, 3, 4, 5, 6, 7, 8, 9, or 10 nucleotides, preferably variants that are effective in reproductively sterilizing fish upon contact with fish egg(s). SEQ ID NO:2 is a preferred variant of SEQ ID NO: 1.

Variants that are effective in reproductively sterilizing fish upon contact with fish egg(s) as used in such context means use of the variants in the methods disclosed herein will result in reproductively sterile fish. In embodiments, the variants will effectively suppress the expression of a dead end gene of interest.

According to embodiments of the methods of the disclosure, unfertilized fish egg(s) (one or more eggs) are immersed in an immersion medium comprising an antisense Morpholino oligomer capable of effectively suppressing the expression of a dead end gene in the fish of interest. The concentration of the antisense Morpholino oligomer in the bath should be sufficient to allow the antisense Morpholino oligomer to traverse the chorion of the fish egg(s), effectively transfecting the egg(s). In embodiments, such concentration will typically be about 1 to about 20, more preferably, about 3 to about 15 and still more preferably, about 5 to about 10 μM.

The immersion media is an aqueous medium which may further comprise fish ovarian fluid or fertilization diluent that contains salt, Tris (pH 7-9), Glycine, and/or 0 to 30% of serum and protease inhibitors such as aprotinin or leupeptin.

Although the time required for the immersion of the unfertilized eggs or pre-water-activated fertilized eggs to result in satisfactory sterilization of the fish and other egg-producing aquatic animals will depend on the species of fish and other egg-producing aquatic animals, typically the fish or other eggs will be immersed in the immersion media containing a Morpholino oligomer for about 2 to about 96 hours, more preferably for about 4 to about 72 hours, and still more preferably from about 5 to about 48 hours.

The present disclosure further relates to methods for the production of reproductively sterile fish and other egg-producing aquatic animals for aquaculture, the aquarium trade, and control of invasive species wherein the methods include disruption of gonadal development through the administration of molecular transporter-conjugated compounds to the egg or embryos, by which the compounds are able to transfect the egg(s), i.e., reach and enter either unfertilized eggs or embryos. The action of the compounds inside of the egg or embryos leads to the failure of fertile gonad development and ultimately to the production of sterile adult fish and other egg-producing aquatic animals. The molecular transporter is able to effectively transport the compounds conjugated to it through miniscule channels and pores, thereby allowing chemicals, drugs, peptides etc. to pass through the chorion and enter the egg or embryo and reach the target tissue. Thus, via these methods, eggs, either unfertilized or fertilized, may be effectively contacted with Morpholino oligomers (or other biologically beneficial compounds) to produce reproductively sterile fish and other egg-producing aquatic animals.

In one aspect, the disclosure relates to methods of producing reproductively sterile fish and other egg-producing aquatic animals by administration of molecular transporter-conjugated compounds to either unfertilized fish eggs or embryos in order to disrupt gonadotropin releasing hormone (GnRH) cell development and/or primordial germ cell (PGC) development and migration to, and colonization in, the gonad of the embryo, which results in the failure of gonad development and/or the failure of full and proper gonadal functioning at the cellular or tissular level, and ultimately the generation of sterile fish and other egg-producing aquatic animals.

The molecular transporter entity may be any compound capable of conjugating a Morpholino oligomer for delivery of the Morpholino oligomer to eggs or embryos.

In one aspect, the disclosure relates to a molecular transporter comprising dendrimeric oligoguanidine with a triazine core, e.g., of a type as described in U.S. Pat. No. 7,935,816. Such molecular transporter may be an octaguanidine dendrimer with a triazine core, also known in the art as "Vivo". The disclosure of U.S. Pat. No. 7,935,816 is hereby incorporated herein by reference in its respective entirety.

An illustrative octaguanidine dendrimer transporter compound with morpholino as a representative bioactive substance is shown in the following conjugate:

A particular precursor transporter compound that is useful with morpholino oligomers of the disclosure is 2-[(4-nitrophenyl)oxycarbonylhexamethylenecarbonylpiperazinyl]-4,6-bis{di-[di(trifluoroacetamidohexyl)aminocarbonyloxyethyl]amino}triazine.

The disclosure further relates to the use of an octaguanidine dendrimer with a triazine core as a molecular transporter to enable traversal by large bio-active molecules or biologically beneficial compounds across the chorion of eggs. Such molecular transporter is effective for chorionic transport of a conjugate of the molecular transporter compound and Morpholino oligomer.

In another aspect of the disclosure, methods are provided for delivery of compounds into egg(s) from egg-producing aquatic animals comprising contacting unfertilized or pre-water-activated egg(s) with at least one biologically beneficial compound. According to these methods, the unfertilized or pre-water-activated egg(s) are sufficiently permeable to effectively uptake the at least one biologically beneficial compound. "Effectively uptake" as used herein means that the biologically beneficial compound will be effective for the beneficial effect intended by use thereof. The biologically beneficial compound may be selected from the group consisting of antibodies, proteins, peptides, RNAs and DNAs.

In embodiments, the biologically beneficial compound will be provided as a conjugate of a biologically beneficial compound and a molecular transporter compound comprising an octaguanidine dendrimer comprising a triazine core moiety. In these embodiments the molecular transporter compound is effective for chorionic transport of the biologically beneficial compound such that the contacting comprises chorionic transfection of the egg(s). The biologically beneficial compound, in embodiments providing the compound in a conjugate form, is a compound which can form a conjugate with the molecular transporter compound comprising an octaguanidine dendrimer comprising a triazine core moiety. The biologically beneficial compound may be selected from the group consisting of antibodies, proteins, peptides, RNAs and DNAs.

In another aspect, the disclosure provides a method for producing reproductively sterile egg-producing aquatic animals, said method comprising contacting unfertilized egg(s) or pre-water-activated fertilized eggs with anti-sense Morpholino oligomer that is effective to transfect the egg(s) and render individual(s) produced therefrom reproductively sterile, wherein the anti-sense Morpholino oligomer is conjugated with a molecular transporter compound effective for chorionic transport of the conjugate.

In another aspect, the disclosure contemplates a method for producing reproductively sterile egg-producing aquatic animals, said method comprising contacting fertilized egg(s) (or embryos) with anti-sense Morpholino oligomer conjugated with a molecular transporter compound that is effective to transfect the egg(s) and render individual(s) produced therefrom reproductively sterile.

The selected oligomers may disrupt GnRH cell and/or PGC development, migration and/or survival in large numbers of embryos, resulting in large-scale production of reproductively sterile adult fish and other egg-producing aquatic animals. The methods of the disclosure are also applicable to single embryos in smaller scale production of reproductively sterile adult fish and other egg-producing aquatic animals.

In embodiments, the methods include preparation and use of a molecular transporter conjugated with an antisense Morpholino oligomer capable of effectively suppressing the expression of dnd, nanos or vasa in fish species and other egg-producing aquatic animals. In other embodiments, the antisense Morpholino oligomer is capable of effectively suppressing the expression of at least one of Salmonidae dead end gene, Moronidae dead end gene or cichlid dead end gene. In further embodiments, the antisense Morpholino oligomer is SEQ ID NO: 1, SEQ ID NO: 2, SEQ ID NO: 3, SEQ ID NO: 4 or variants thereof which are capable of effectively suppressing the expression of dead end in fish species.

In one embodiment, a method for producing reproductively sterile egg-producing aquatic animals is provided, comprising immersing unfertilized or fertilized fish egg(s) in an immersion media comprising a conjugate of a molecular transporter compound and an antisense Morpholino oligomer capable of effectively suppressing expression of the dead end gene or other genes such as nanos, vasa, gnrh or fsh receptor that are essential for gonadal development in the fish and other egg-producing aquatic animals. Preferably, the molecular transporter is an octaguanidine dendrimer with a triazine core.

According to particular aspects of the methods of the disclosure, unfertilized egg(s) or pre-water-activated egg(s) (one or more) are immersed in an aqueous medium comprising an antisense Morpholino oligomer or an antisense Morpholino oligomer-transporter conjugate capable of effectively suppressing the expression of a dead end gene or other genes that are essential for gonadal development in the fish and other egg-producing aquatic animals. The concentration of the antisense Morpholino oligomer in the bath should be sufficient to allow the antisense Morpholino oligomer-transporter conjugate to traverse the chorion of the egg(s). In embodiments, such concentration will typically be about 1 to about 20 more preferably about 3 to about 15 even more preferably from about 5 to about 10 µM.

Alternatively, the disclosure contemplates a method for producing reproductively sterile egg-producing aquatic animals, said method comprising contacting fertilized egg(s) with anti-sense Morpholino oligomer conjugated with a molecular transporter compound that is effective to transfect the fertilized egg(s) and render individual(s) produced therefrom reproductively sterile. The contacting comprises chorionic transfection of the egg(s).

In embodiments of this method, fertilized eggs (embryos) are treated by immersion in an immersion medium comprising an antisense Morpholino oligomer-transporter conjugate capable of effectively suppressing the expression of a dead end gene or other genes that are essential for gonadal development in the fish and other egg-producing aquatic animals of interest. The concentration of the antisense Morpholino oligomer in the bath should be sufficient to allow the antisense Morpholino oligomer-transporter conjugate to traverse the chorion of the fertilized egg(s). Such concentration will be higher than the amount needed for immersion of unfertilized fish egg(s) since, after fertilization and water-activation, the egg chorion becomes impermeable, hindering traversal into the egg. Typically, the concentration of the bath for immersion of embryos is about 20 to about 80 preferably about 40 to about 60 µM.

In embodiments of the treatment of fertilized eggs, the antisense Morpholino oligomer is capable of effectively suppressing the expression of at least one of Salmonidae dead end gene, Moronidae dead end gene or cichlid dead end gene. In further embodiments, the antisense Morpholino oligomer is SEQ ID NO: 1, SEQ ID NO: 2, SEQ ID NO: 3, SEQ ID NO: 4 or a variant thereof which is capable of effectively suppressing the expression of dead end in the fish species and other egg-producing aquatic animals.

In another aspect of the disclosure, a composition effective for disruption of primordial germ cell migration in fish is provided, comprising an antisense Morpholino oligomer selected from SEQ ID NO: 1, SEQ ID NO: 3 and SEQ ID NO: 4 or variants such as SEQ ID NO: 2 thereof which are capable of effectively suppressing expression of the dead end gene in fish. In such aspect, a composition for treatment of fish egg(s) to render fish produced therefrom reproductively sterile is provided, comprising an anti-sense Morpholino oligomer comprising an oligomer selected from the group consisting of oligomers of SEQ ID NOS: 1-4 and variants thereof that are effective in reproductively sterilizing fish upon contact with fish egg(s). This Morpholino oligomer composition preferably is used in treatment of unfertilized fish egg(s).

The disclosure further relates to a novel compound entity that is able to specifically disrupt gonadal development resulting in the production of infertile fish. The new compound entity comprises an octaguanidine dendrimer molecular transporter conjugated to a Morpholino antisense oligomer that effectively suppresses the translation of dead end, an essential protein for germ cell survival, mRNA. Such conjugate may be used for treating unfertilized or pre-water-activated eggs or for treating fertilized eggs.

Such conjugated compounds may be used for the production of sterile fish and other egg-producing aquatic animals. The morpholino oligomer compounds can be conjugated to the molecular transporter to effectively traverse the chorion and enter the embryos. Hence, the compounds are able to specifically disrupt gonadal development resulting in the generation of infertile fish and other egg-producing aquatic animals. Preferably, the molecular transporter comprises an octaguanidine dendrimer with a triazine core and the oligomer comprises an antisense Morpholino oligomer selected from SEQ ID NO: 1, SEQ ID NO: 3 and SEQ ID NO: 4 or any of various variants that are effective in reproductively sterilizing fish upon contact with fish egg(s), such as SEQ ID NO: 2.

It will be recognized that the contacting of eggs and/or embryos with the compounds, conjugates, and compositions of the present disclosure may be carried out in any suitable manner, e.g., involving immersion contacting, or alternatively by contacting not involving immersion, although it is to be recognized that immersion contacting provides an efficient and effective contacting technique that is amenable to large-scale operations for the production of reproductively sterile fish and aquatic animals. Non-immersion contacting techniques that may be utilized in the broad practice of the present disclosure include, without limitation, spray or drip methods for contacting, dry transfer techniques, in which eggs are contacted with a carrier or surface coated with or otherwise supporting any of the compounds, conjugates, or compositions of the present disclosure that are effective for production of reproductively sterile fish, or other techniques by which the eggs and/or embryos are contacted with the compounds, conjugates, and/or compositions of the present disclosure. The contacting preferably comprises a non-injection contacting.

The advantages and features of the disclosure are further illustrated with reference to the following examples, which are not to be construed as in any way limiting the scope of the disclosure but rather as illustrative of particular embodiments of the disclosure in specific applications thereof.

Example 1

Zebrafish were selected for initial exemplification of the methods of the disclosure, due to their short generation time and large numbers of embryos produced per mating, which are easily obtained on a daily or weekly basis. Additionally, the embryos of zebrafish are transparent, providing ease of visual observations, and are hardy. The normal development of GnRH cells, PGCs and gonads within the embryo is an evolutionarily conserved mechanism that is found in all fish. Accordingly, the methods of the disclosure are applicable to all fish species, including, but not limited to, zebrafish, carp species, trout species, salmon species, breams (including seabreams and porgies), basses (including marine and freshwater seabass and hybrid basses, etc), perches (yellow perch, white perch, etc), catfish species, cod and other major classes that are candidates for captive culture.

Vivo and dnd-MO

Figure 3:
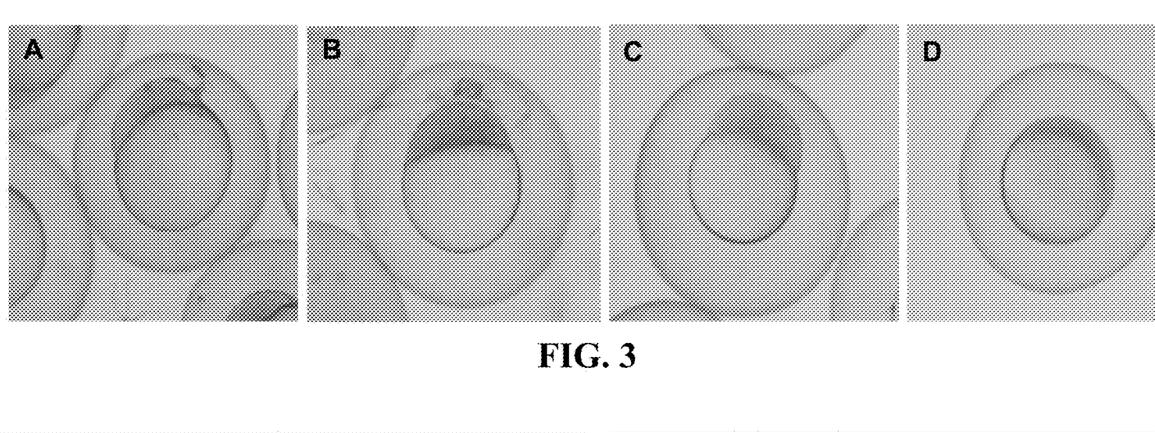
FIG. 3 is a photomicrograph showing the results of the immersion of zebrafish embryos in an immersion bath of the molecular transporter Vivo conjugated to dnd-MO. In FIG.

A molecular transporter, a dendrimeric octaguanidine with a triazine core also known as Vivo, was conjugated to zebrafish dnd-MO, 5'-GCTGGGCATCCATGTCTCCGAC-CAT-3' (SEQ ID NO 5) (zfdnd-MO-Vivo) and used in an immersion containing zebrafish embryos in water. After a 3-hour immersion with 20 µM of zfdnd-MO-Vivo, uncharacterized aggregates were found around the inner part of chorion or the surface of the blastodisc of the embryos (FIG. 3A). More aggregates appeared after a 5-hour immersion (FIG. 3B). These aggregates were not seen in the non-conjugated control groups that immersed with 20 µM of zfdnd-MO for 3 (FIG. 3C) or 5 (FIG. 3D) hours. The results indicated that conjugation of the antisense Morpholino oligomers with Vivo provided the ability of the conjugated compound to act on chorion that caused aggregates.

Figure 4:
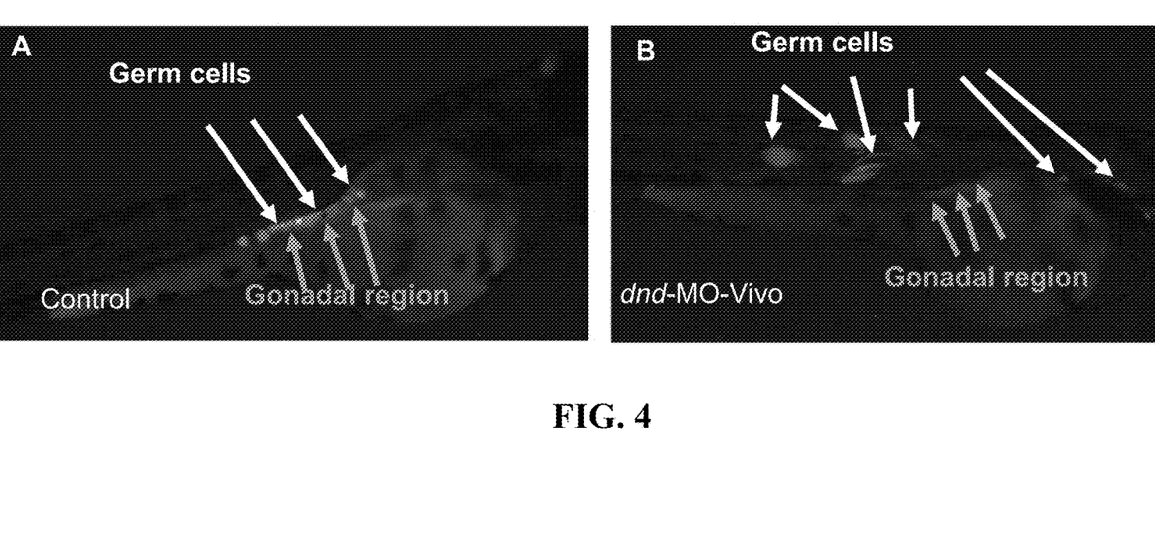
FIG. 4 is a fluorescence photomicrograph showing the effects of the administration to fish embryos of a molecular transporter conjugated to an antisense Morpholino oligomer (MO) that effectively blocks the translation of Dead end (Dnd) protein.

At 2 days post-fertilization, fluorescence microscopy examination revealed that germ cells in the embryos immersed with 40 or 60 µM zfdnd-MO-Vivo had mis-migrated and differentiated to other cell types (FIG. 4A, FIG. 4B). As shown, zebrafish dnd-MO-Vivo disrupted germ cell development in zebrafish. FIG. 4A shows that in control fish, germ cells migrated to the gonadal region and maintained their morphology (round-shape cells). FIG. 4B shows that that treatment of zfdnd-MO-Vivo caused germ cell mis-migration and eventual differentiated into other cell types.

Example 2

Figure 5:
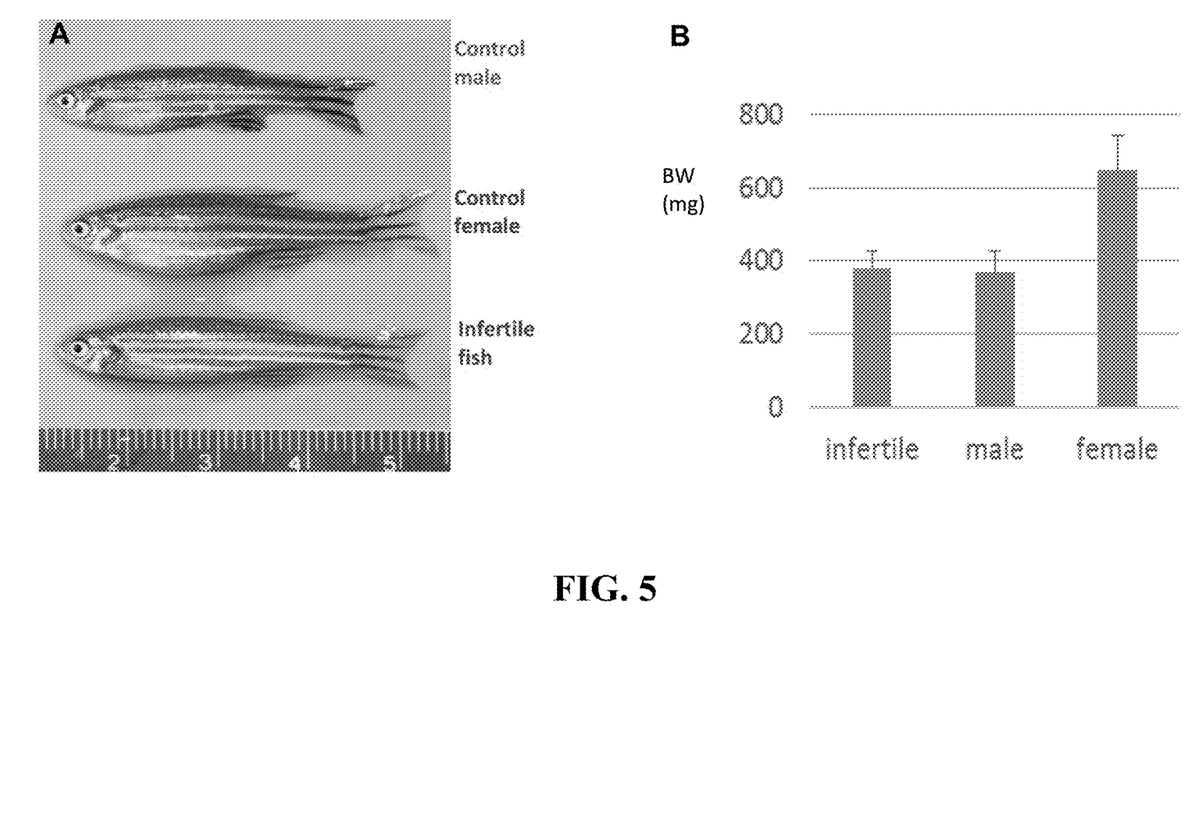
FIG. 5 is a photograph and graphical representation showing zebrafish dnd-MO-Vivo treated embryos developed into infertile male-like adults.
Figure 8:
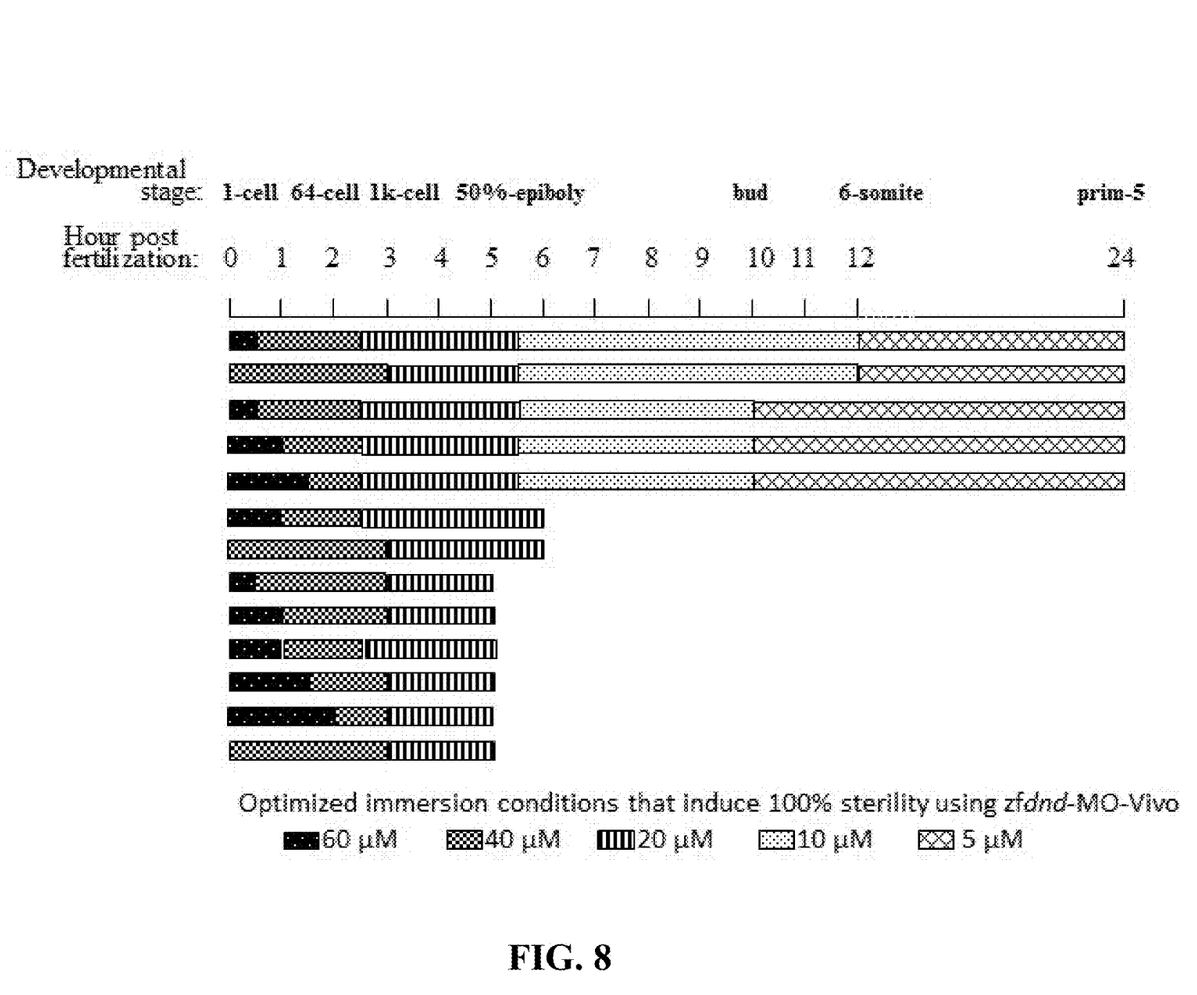
FIG. 8 is a graphical representation of zebrafish dnd-MO-Vivo treated embryos developed into infertile adults. In several optimized conditions, when the immersion was initiated immediately after fertilization and lasted to both 24 hour (or prim-5 stage) and 5 to 6 hour (or 50%-epiboly stage), all the embryos that were initially immersed with 60 or 40 μM of zfdnd-MO-Vivo developed into infertile fish.

The zebrafish treated in Example 1 were examined after development into adult fish. The bath immersion of zebrafish embryos with 40 or 60 µM zfdnd-MO-vivo allowed for efficiently inducing 100% sterility in the individuals that were treated under optimal conditions as shown in FIG. 8, without affecting any other physiological characteristics of the fish (FIG. 5). As shown in FIG. 5, zebrafish dnd-MO-Vivo treated embryos developed into infertile male-like adults. FIG. 5A shows no difference in appearance or overall size observed between treated adult fish and wild-type males. FIG. 5B shows no significant difference in body-weight of 3-month-old fish (n=12 by random sampling) among zfdnd-MO-Vivo treated fish, and untreated wild-type males.

Figure 6:
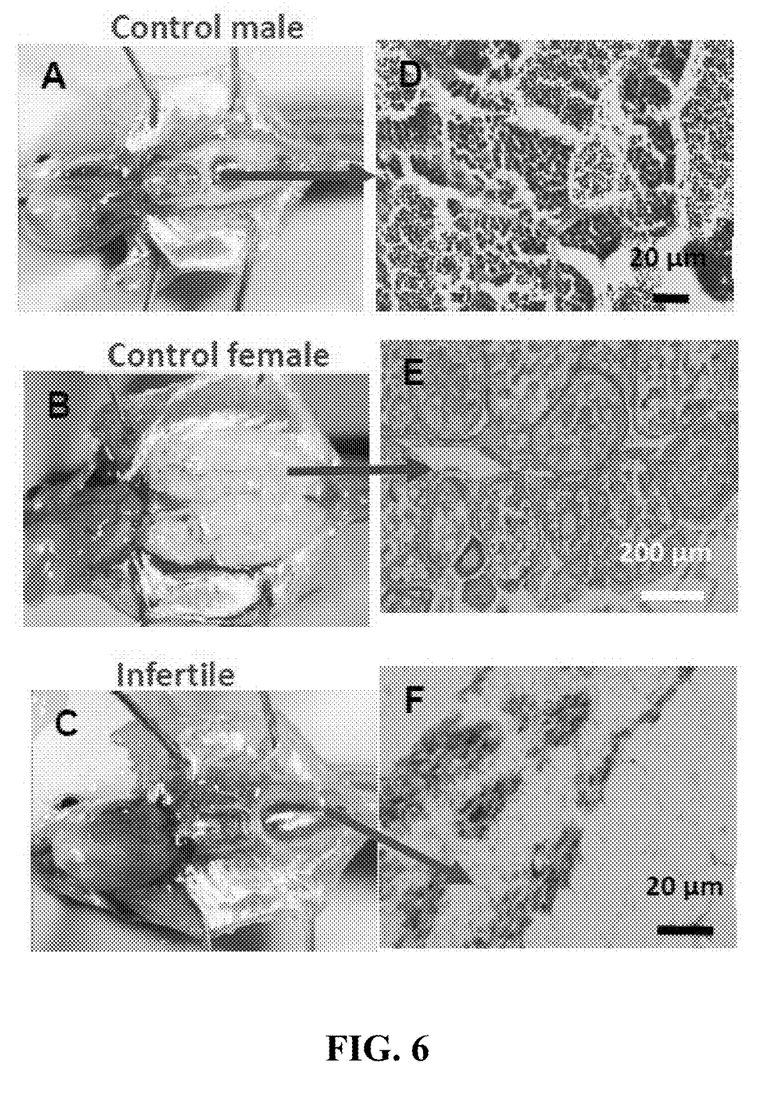
FIG. 6 is a photomicrograph showing zfdnd-MO-Vivo induced sterility in zebrafish. Examination of gonadal tissue show (FIG. 6A) well-developed testis of untreated male fish.
Figure 7:
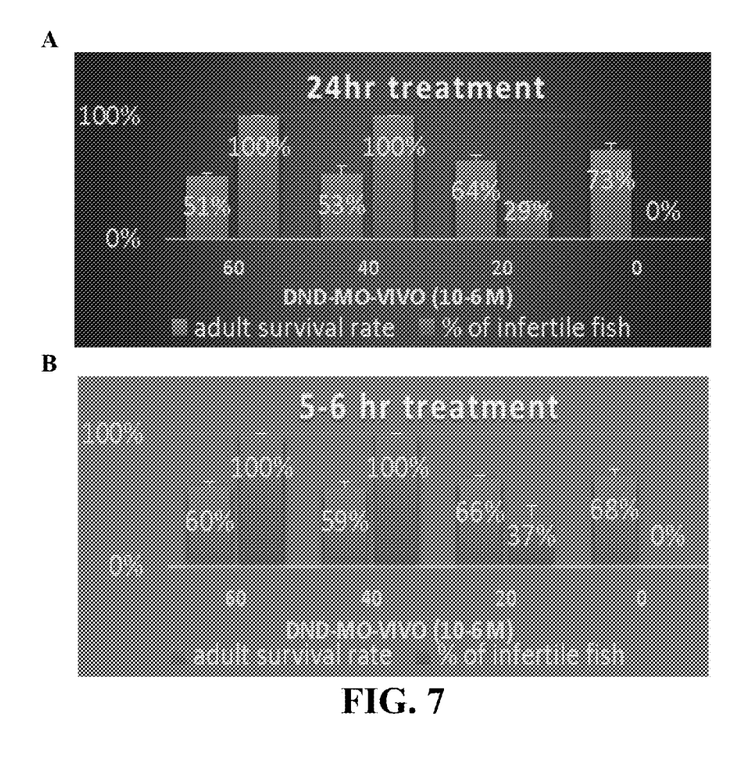
FIG. 7 is a graphical representation of zebrafish dnd-MO-Vivo treated embryos developed into infertile adults. In both FIG. 7A, 24 hour, and FIG. 7B, 5 to 6 hour immersions, all the embryos that were initially immersed with 60 or 40 μM of zfdnd-MO-Vivo developed into infertile fish.

In additional experiments, the methods of the disclosure were successfully applied to zebrafish and the duration of immersion was decreased to 5 to 6 hours without affecting the efficiency of sterility (FIG. 6 FIG. 7, and FIG. 8). In FIG. 6, zfdnd-MO-Vivo induced sterility in zebrafish is shown. Examination of gonadal tissue showing (A) A well-developed testis of untreated male fish. (B) A well-developed ovary of untreated female fish. (C) The gonads of zfdnd-MO-Vivo treated fish developed into a thin filament-like tissue. Photomicrographs (D-F) show (D) active spermatogenesis of the testis of untreated male fish. (E) A well-developed ovary of an untreated female fish with oocytes at different developmental stages. (F) The gonad of treated fish appears to be under-developed and surrounded with a large amount of adipocytes without advanced gonadal structure or germ cells.

As shown in FIG. 7 and FIG. 8, zebrafish dnd-MO-Vivo treated embryos developed into infertile adults. In both A) 24 hour and B) 5 to 6 hour immersions, all the embryos that were initially immersed with 60 or 40 µM of zfdnd-MO-Vivo immediately after fertilization developed into infertile fish.

Example 3

Figure 9:
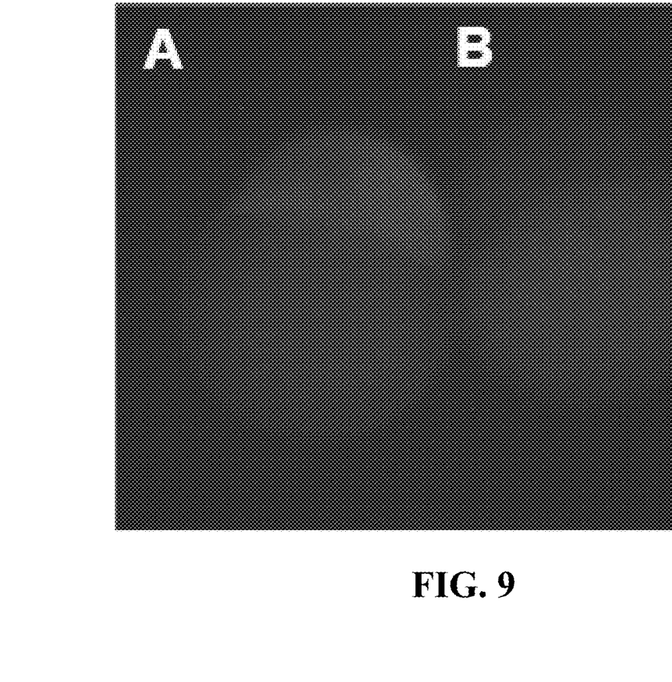
FIG. 9 is a photomicrograph showing that eggs are more permeable before water activation. In a 5 hour immersion with 40 μM of zfdnd-MO-Flu, shown in FIG. 9A, unfertilized eggs up-take more zfdnd-MO-Flu (stronger green fluorescence) than as shown in FIG. 9B, pre-water-activated eggs.

To continuously optimize the technology, the bath immersion was conducted using unfertilized eggs since the permeability of the chorion gradually decreases after fertilization and water activation. Our results show that when eggs were immersed with 40 µM fluorescein labelled zfdnd-MO (dnd-MO-Flu), the unfertilized eggs up-took more dnd-MO-Flu than the eggs were water-activated 1 hour before immersion (FIG. 9). As shown in FIG. 9, eggs are more permeable before water activation. In a 5 hour immersion with 40 µM of zfdnd-MO-Flu, A) unfertilized eggs up-take more zfdnd-MO-Flu (stronger green fluorescence) than B) pre-water-activated eggs.

Example 4

Figure 10:
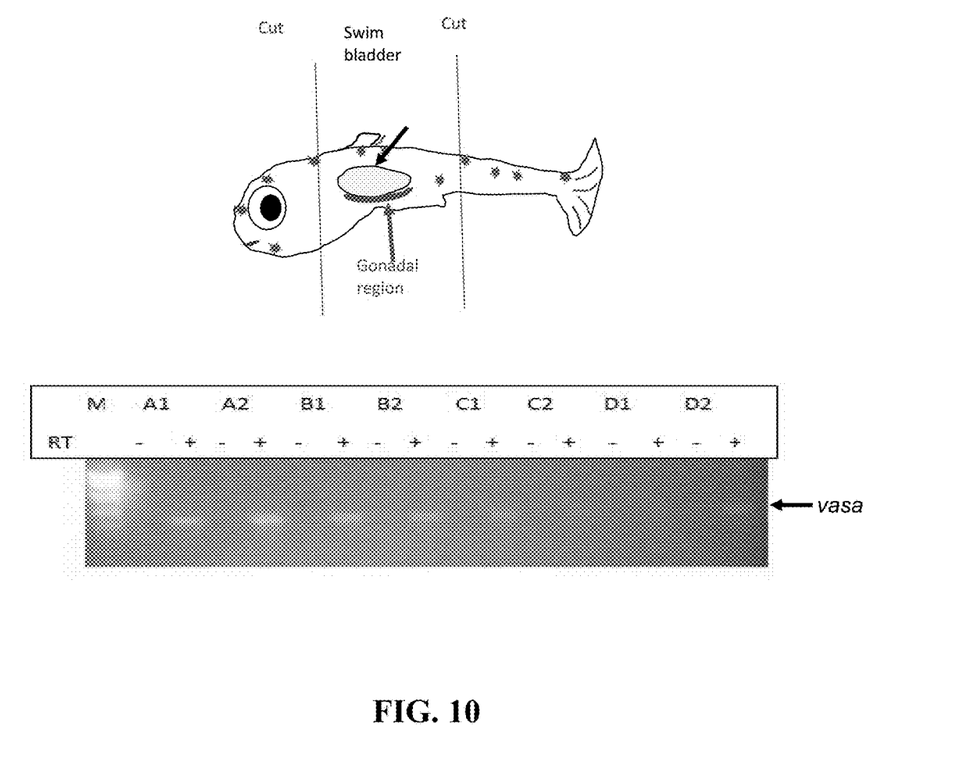

When pre-fertilized salmonids (trout) eggs were immersed with salmonid's dnd-MO+dnd-MO-Vivo (Ssdnd-MO+Ssdnd-MO-Vivo), germ cells were eliminated (FIG. 10) indicated by the lack of expression of germ cell specific maker gene vasa. As shown in FIG. 10, Salmonids (trout) eggs were immersed with salmonid's dnd-MO at A: Control; B: 10 µM Ssdnd-MO; C: 10 µM Ssdnd-MO+1 µM Ssdnd-MO-Vivo; D: 10 µM Ssdnd-MO+2 µM Ssdnd-MO-Vivo for 48 hours before fertilization. Soon after hatch, the middle part of body was cut and used for RNA extraction and RT-PCR for detecting vasa expression. One fish from group C and one from group D appeared to have very low vasa expression, indicating possible effect on reducing germ cell abundance. RT: reverse transcription.

As described herein, the methods are generally applicable to farmed fish and aquatic egg-producing animals, as production of sterile farmed species is desirable. Accordingly, the methods of the invention are applicable to any farmed species of fish and aquatic egg-producing animals, particularly to commercially important farmed species.

While the disclosure has been has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

INDUSTRIAL APPLICABILITY

The methods and compounds of the disclosure produce reproductively sterile fish and aquatic egg-producing animals. Sterilization (induced infertility) of farmed fish and aquatic egg-producing animals enhances their growth rate by increasing the conversion of food energy to muscle growth, instead of gonadal development. In addition, if escaped from aquaculture operations to the environment, reproductively sterile farmed fish and egg-producing aquatic animals, including domesticated, non-native or genetically modified species, will not be able to reproduce or inter-breed with wild stock. This will assist biological containment and prevent genetic contamination of wild populations and/or the establishment in the wild of domestic, non-native or genetically modified farmed fish and aquatic egg-producing animals.

What is claimed is:

1. A composition for treatment of fish eggs to render fish produced therefrom reproductively sterile, said composition comprising an anti-sense Morpholino oligomer conjugated to an octaguanidine dendrimer molecular transporter, wherein said anti-sense Morpholino oligomer suppresses the translation of dead end gene in said fish.

2. The composition of claim 1, wherein said anti-sense Morpholino oligomer comprises an oligomer selected from the group consisting of oligomers of SEQ ID NOS: 1-4 and variants thereof.

3. The composition of claim 1, comprising an aqueous medium containing the anti-sense Morpholino oligomer.

4. The composition of claim 1 wherein the fish eggs are unfertilized or pre-water-activated fertilized fish eggs.

5. The composition of claim 4, wherein the concentration of the anti-sense Morpholino oligomer is in a range of from 1 to 20 µM.

6. The composition of claim 4, wherein the concentration of the anti-sense Morpholino oligomer is in a range of from 3 to 15 µM.

7. The composition of claim 4, wherein the concentration of the anti-sense Morpholino oligomer is in a range of from 5 to 10 µM.

8. The composition of claim 1, wherein the fish eggs are fertilized fish eggs.

9. The composition of claim 8, wherein the concentration of the anti-sense Morpholino oligomer is in a range of from 20 to 80 µM.

10. The composition of claim 8, wherein the concentration of the anti-sense Morpholino oligomer is in a range of from 40 to 60 µM.

11. The composition of claim 1, wherein the anti-sense Morpholino oligomer is conjugated with 2-[(4-nitrophenyl) oxycarbonylhexamethylenecarbonylpiperazinyl]-4,6-bis {di [di(trifluoro-acetamidohexyl)-aminocarbonyloxyethyl] amino}triazine.

12. The composition of claim 1, wherein the anti-sense Morpholino oligomer comprises an oligomer selected from the group consisting of oligomers of SEQ ID NOS: 1-4.

13. The composition of claim 12, wherein the anti-sense Morpholino oligomer comprises an oligomer of SEQ ID NO: 1.

14. The composition of claim 12, wherein the anti-sense Morpholino oligomer comprises an oligomer of SEQ ID NO: 2.

15. The composition of claim 12, wherein the anti-sense Morpholino oligomer comprises an oligomer of SEQ ID NO: 3.

16. The composition of claim 12, wherein the anti-sense Morpholino oligomer comprises oligomer of SEQ ID NO: 4.

17. The composition of claim 1, wherein the anti-sense Morpholino oligomer is SEQ ID NO: 1, SEQ ID NO: 2, SEQ ID NO: 3, SEQ ID NO: 4 or a variant thereof.

18. The composition of claim 17, wherein the anti-sense Morpholino oligomer is SEQ ID NO: 1 or a variant thereof.

19. The composition of claim 17, wherein the anti-sense Morpholino oligomer is SEQ ID NO: 2 or a variant thereof.

20. The composition of claim 17, wherein the anti-sense Morpholino oligomer is SEQ ID NO: 3 or a variant thereof.

21. The composition of claim 17, wherein the anti-sense Morpholino oligomer is SEQ ID NO: 4 or a variant thereof.

22. The composition of claim 1, wherein the anti-sense Morpholino oligomer conjugated to the octaguanidine dendrimer molecular transporter is effective in reproductively sterilizing said fish eggs by the fish eggs being immersed in an immersion medium comprising an effective amount of said anti-sense Morpholino oligomer conjugated to said octaguanidine dendrimer molecular transporter.

* * * * *